US006914680B2

(12) United States Patent
Kawate

(10) Patent No.: US 6,914,680 B2
(45) Date of Patent: Jul. 5, 2005

(54) OPTICAL SYSTEM FOR MEASUREMENT OF OPTICAL CONSTANT

(75) Inventor: Etsuo Kawate, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 309 days.

(21) Appl. No.: 10/255,940

(22) Filed: Sep. 27, 2002

(65) Prior Publication Data

US 2004/0008346 A1 Jan. 15, 2004

(30) Foreign Application Priority Data

| Jul. 9, 2002 | (JP) | ......................................... 2002-199496 |
| Jul. 9, 2002 | (JP) | ......................................... 2002-199588 |

(51) Int. Cl.$^7$ .............................. G01J 1/00; G01N 21/55; G01N 21/59
(52) U.S. Cl. ....................... 356/434; 356/325; 356/445; 356/448
(58) Field of Search ................................. 356/319, 323, 356/325, 51, 434, 440, 445, 447, 448

(56) References Cited

U.S. PATENT DOCUMENTS

| 3,402,634 A | * | 9/1968 | Bennett ....................... 356/323 |
| 3,499,716 A | * | 3/1970 | Bennett ....................... 356/445 |
| 3,687,519 A | * | 8/1972 | Mapes ......................... 356/73 |
| 6,128,093 A | * | 10/2000 | Niikura ....................... 356/319 |

* cited by examiner

*Primary Examiner*—F. L. Evans
(74) *Attorney, Agent, or Firm*—Oblon, Spivak, McClelland, Maier & Neustadt, P.C.

(57) ABSTRACT

An optical system for determining an optical constant by measuring the absolute reflectance and the absolute transmittance of a substance by using an incoming side beam switching mirror for selectively switching the direction of a light from a light source to first or second converged light reflecting units. The first and second converged light reflecting units project the light from the beam switching mirror so as to be converged in an intersecting manner at the position of a sample holder that can be positioned to present a sample fitting hole or a through hole for measuring the reflectance/transmittance by providing the light to an exit side beam switching mirror and detector.

11 Claims, 12 Drawing Sheets

OPTICAL SYSTEM FOR MEASUREMENT OF OPTICAL CONSTANT

TECHNICAL FIELD OF THE INVENTION

The present invention relates to an optical system for measurement of optical constant capable of measuring the absolute reflectance and the absolute transmittance, and in particular, it relates to an optical system capable of measuring both the absolute reflectance for the face side incidence and the back side incidence and the absolute transmittance for the face side incidence and the back side incidence by allowing the light to be incident on the sample, and, in addition, being built in a system comprising an external light source such as a laser beam and a microwave light source and a detector, or a dispersion type spectrophotometer or a Fourier transformation type spectrophotometer.

DESCRIPTION OF THE RELATED ART

Optical technology is utilized in high-speed large-capacity optical communication, image processing, etc. in the IT industry, a laser knife, cancer treatment, etc. in the medical industry, the nano-technology, isotope separation, a display, an illumination appliance, etc. using laser beam in the manufacturing industry, and precise optical measurement, information processing technology development, etc. in the academic field, and is a very important technology in modern life.

The basic technology for supporting this optical technology is determination of the optical constant (the refractive index and the attenuation coefficient) of the substance, in other words, the complex dielectric constant. Two independent measurements are necessary to determine these two unknowns (the refractive index and the attenuation coefficient).

One of the methods is to determine the optical constant by measuring the absolute reflectance and the absolute transmittance at one predetermined angle, and solving the simultaneous equations thereof in a case of a transparent sample such as dielectric, or to determine the optical constant by measuring the absolute reflectance at two different angles of incidence, and solving the simultaneous equations thereof in a case of a non-transparent sample such as metal. These methods are intuitive, and versatile.

Different optical systems have been employed in the measurement of the reflectance and the transmittance of a sample in a conventional dispersion type spectrophotometer for visible and ultraviolet ray range, and a conventional Fourier transformation type spectrophotometer for infrared ray range. Thus, in order to measure two quantities (reflectance and transmittance), troublesome "replacement" of a part of the optical system is necessary at least during the measurement. In addition, this "replacement" causes a considerable error factor in the result of measurement.

In addition, more specifically, the absolute transmittance is determined as the ratio of the light intensity according to presence and absence of a sample on the axis of the incoming light. In this case, the sample and a detector may be disposed in a row on the optical axis of the incoming light, and the measurement is easy. On the other hand, the measurement of the absolute reflectance is determined as the ratio of the light intensity according to the presence and absence of the sample. In this case, if the sample is absent, the light passes in the direction of the incoming light. On the other hand, if the sample is present, the passing direction of the reflected light is different from the original direction of the incoming light due to the reflection.

For the measurement of this absolute reflectance, a method (goniometric method) for moving the detector, and a method (V-N method and V-W method) for moving an additional mirror while the detector is fixed have been developed.

FIGS. 12A and 12B describe a method for measuring the absolute reflectance by a conventional goniometric method. In this goniometric method, the exiting light from a light source LS of a spectrophotometer, etc. is converged at a sample holder SH, and the transmitted or reflected light is detected by a detector D. The sample holder SH has a through hole B and a sample T, and slides to select either of them.

In the measurement, as shown in FIG. 12A, the through hole B is selected by the sample holder SH, and the background signal is measured by the detector D. The angle of incidence in this state is defined as θ. Next, the sample holder SH is allowed to slide to select the sample T, the detector D is turned around the sample by (180°−2θ), and the sample signal reflected by the sample is measured (refer to FIG. 12B). By calculating the ratio to the background signal, the absolute reflectance to the angle of incidence q can be determined.

In this goniometric method, the absolute transmittance can also be measured. In this case, as shown in FIG. 12A, the through hole B is selected in the sample holder SH, and the background signal is measured by the detector D similarly to the above. Next, the sample holder SH is allowed to slide to select the sample T, and the detector D can measure the sample signal transmitted through the sample T substantially at the same place. The absolute transmittance to the angle of incidence θ is determined as the ratio of these two quantities.

In the measurement of the absolute reflectance, the detector or the mirror must be moved. Reproducibility of the movement of this detector or the mirror considerably influences the measurement errors.

As described above, in the conventional measurement of the absolute reflectance, generally speaking, the measurement accuracy is poor, and the accuracy is about several % in the measurement of the absolute reflectance using a spectrophotometer on the market.

In addition, in the goniometric method, the absolute reflectance can be measured at an arbitrary angle of incidence while the angle of incidence cannot be generally changed in other V-W method or V-N method.

Regarding the measurement of the light scattering from the sample, the detector is moved at the angle other than that of the regular reflection from the sample in the goniometric method, or the sample is set in an integrating sphere and the regularly reflected light is allowed to escape outside the integrating sphere by a method using the integrating sphere. In this method using the integrating sphere, only the mean light scattering is determined, and the angle dependency of the light scattering by the sample can be determined by the goniometric method in principle, but the measurement is very difficult.

SUMMARY OF THE INVENTION

An object of the present invention is to solve these conventional problems, and more specifically, to provide an optical system for measurement of optical constant capable of measuring the absolute reflectance and the absolute transmittance by eliminating factors for large errors of the measurement result without using any different optical systems for measurement of the reflectance and the transmittance of the sample, and unnecessary to "replace" a part of the optical system during the measurement in order to measure the absolute reflectance and the absolute transmittance.

Another object of the present invention is to provide an optical system for measurement of optical constant which can be easily built in a dispersion type spectrophotometer extensively used in the wavelength range shorter than the wavelength of near infrared rays, or a Fourier transformation type spectrophotometer used in the wavelength range longer than the wavelength of near infrared rays.

Still another object of the present invention is to provide an optical system for measurement of optical constant capable of easily measuring the absolute reflectance and the absolute transmittance of a substance with excellent accuracy not only in the system comprising an external light source such as a laser beam or microwave light source and a detector, but also in the dispersion type spectrophotometer and Fourier transformation type spectrophotometer.

Still another object of the present invention is to provide an optical system for measurement of optical constant capable of measuring the absolute reflectance and the absolute transmittance for the face side incidence and the back side incidence by allowing the light to be incident on a sample from a face side and a back side, respectively.

Still another object of the present invention is to provide an optical system for measurement of optical constant capable of measuring the reflectance and the transmittance at an arbitrary angle of incidence, and measuring the spectrum not influenced by multiple reflection within a substrate in a composite sample such as a thin film on the substrate.

Still another object of the present invention is to provide an optical system for measurement of optical constant capable of measuring also light scattering by a sample.

Basically, the optical system for measurement of optical constant in accordance with the present invention to achieve the above objects is characterized in that first and second optical paths intersected on the sample holder are set, the sample fitting hole or the through hole is selectively positioned by the sample holder by advancing/retracting the sample fitting hole or the through hole to/from an intersection of both optical paths, the first and second optical paths are formed by projecting the light so as to be converged on the intersection from an incoming side beam switching mirror for selectively switching the direction of the light from the light source to the first or second converged light reflecting means side via the first or second converged light reflecting means, first and second received light reflecting means for projecting the light to a single exiting side beam switching mirror are disposed on the optical path of the light reflected by or transmitted through the sample set in the sample fitting hole of the sample holder via the first or second optical path, or the through hole, the exiting side beam switching mirror is capable of switching the direction of the light projected via the received light reflecting means so that the light is projected toward a single detector, and the absolute reflectance and the absolute transmittance for the face side incidence and the back side incidence of the sample can be measured.

In the optical system for measurement of optical constant, the first and second converged light reflecting means and the first and second received light reflecting means are ellipsoidal mirrors, respectively, each of the ellipsoidal mirrors can be disposed so that one focal point is located at the sample holder, the other focal point is on the optical axis of the incoming or exiting light, and the optical axes of the optical paths are within a single plane. In this state, four ellipsoidal mirrors are preferably disposed in an X-shape symmetry to the plane including the sample surface.

In addition, in the optical system for measurement of optical constant in accordance with the present invention, the converged light reflecting means and the received light reflecting means comprise the first and second spheroidal mirrors, and both spheroidal mirrors are coupled with each other at respective apertures thereof so that the axes of rotation and one of focal points are coincident with each, respectively, the sample holder is disposed at the common focal position of the spheroidal mirrors, and the incoming side beam switching mirror and the exiting side beam switching mirror are disposed at two remaining focal positions, and the incoming through hole is opened on the incoming side of the first spheroidal mirror, and the exiting through hole is opened on the exiting side of the second spheroidal mirror, respectively.

In this state, two beam switching mirrors are rotatable in a correlating manner with each other, the absolute reflectance and the absolute transmittance can be measured at an arbitrary angle of incidence, and the beam switching mirror on the exiting side is independently rotatable to measure the light scattering by the sample. In addition, in a case of a composite sample such as the thin film sample on the substrate, the angle of incidence on the sample can be selected to be the Brewster's angle with respect to the substrate by appropriately rotating mainly two beam switching mirrors with the incoming light on the sample being the P-polarized light, and the optical measurement of the thin film not influenced by the multiple reflection within the substrate can be performed.

Further, in the optical system for measurement of optical constant using the first and second spheroidal mirrors, the sample holder can be selectively positioned at the intersection of the optical paths by the sample fitting hole and the reference sample fitting hole, and the reflectance and the transmittance of the sample at an arbitrary angle of incidence can be measured thereby.

Still further, in the optical system for measurement of optical constant of the present invention, the converged light reflecting means and the received light reflecting means are constituted by combining concave mirrors with supplementary mirrors, the concave mirrors and the supplementary mirrors constituting the converged light reflecting means are disposed so that the light from the beam switching mirror on the incoming side is projected on the concave mirror via the supplementary mirror, and projected toward the sample holder, and the concave mirrors and the supplementary mirrors constituting the received light reflecting means are disposed so that the light from the sample holder is projected on the supplementary mirror via the concave mirror, and projected on the beam switching mirror on the exiting side.

In this state, the concave mirrors are preferably disposed in an X-shape symmetry to the plane including the sample surface.

DESCRIPTION OF THE PREFERRED EMBODIMENTS

Embodiments of an optical system in accordance with the present invention will be described in detail with reference to the drawings.

Figure 1:
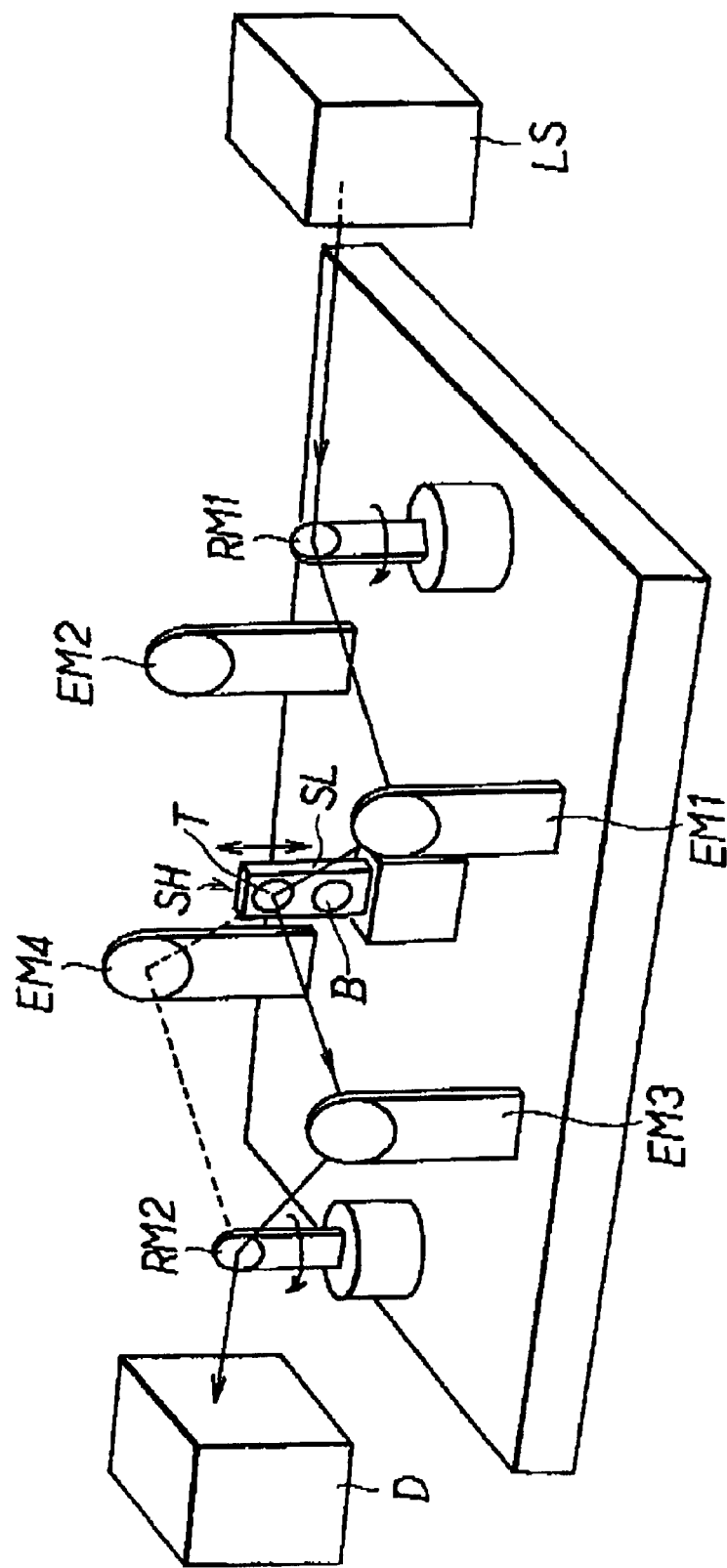
FIG. 1 is a perspective view showing the configuration of a first embodiment of an optical system for measurement of optical constant in accordance with the present invention.

FIG. 1 shows a first embodiment of an optical system for measurement of optical constant in accordance with the present invention. This optical system comprises an incoming side beam switching mirror RM1 and an exiting side beam switching mirror RM2, and four ellipsoidal mirrors EM1, EM2, EM3 and EM4 therebetween, and a sample holder SH is disposed at one focal point of each ellipsoidal mirror.

More specifically, the sample holder SH has a slide member SL with two holes of the same size made therein. One hole is a through hole B without any sample, and the other hole is a sample fitting hole with a sample T fitted thereto so as to completely cover the hole. First and second optical paths across each other are set at the position of this sample holder SH, the slide member SL can be switched by a drive source built in the sample holder SH so that the sample T or the through hole B is placed at an intersection of these optical axes, and the sample fitting hole or the through hole is set retractable at the intersection of these optical paths so as to selectively perform the positioning.

The above four ellipsoidal mirrors EM1, EM2, EM3 and EM4 are disposed in an X-shape symmetry to the place including a sample surface, and each ellipsoidal mirror is disposed so that one focal point is located at the position of the above hole in the sample holder SH, and the other focal point is located on the optical axis of the incoming or exiting light. In the embodiment in the figure, the face side of the sample faces a common plane in contact with the ellipsoidal mirror EM1 and the ellipsoidal mirror EM3, and is placed so as to be parallel to this plane. In addition, the optical axes of optical paths are place so as to be in a single plane.

The incoming side beam switching mirror RM1 selectively switches the direction of the light from a light source LS to the ellipsoidal mirror EM1 constituting a first converged light reflecting means and the ellipsoidal mirror EM2 constituting a second converged light reflecting means, and through this switching operation, the light from the light source LS is projected so as to reach the ellipsoidal mirror EM1 or the ellipsoidal mirror EM2 via a beam switching mirror RM1, and so as to be converged on the sample holder SH via the first or second optical path. The other focal points of the ellipsoidal mirrors EM1 and EM2 with one focal point thereof being located on the sample holder SH are preferably located on the face side of the beam switching mirror RM1, but they may be located on the optical axis of the incoming light toward the ellipsoidal mirrors via the beam switching mirror RM1.

In addition, the ellipsoidal mirrors EM3 and EM4 constituting the first and second received light reflecting means are disposed on the optical path of the light reflected by or transmitted through the sample T set in a sample fitting hole above the sample holder SH or the through hole B via the first or second optical path in a symmetrical manner to the ellipsoidal mirror EM1 and EM2. These ellipsoidal mirrors EM3 and EM4 are disposed to project the light from the sample holder SH toward a single exiting side beam switching mirror RM2, and the exiting side beam switching mirror RM2 can switch the direction thereof so that the light projected via the ellipsoidal mirrors EM3 and EM4 is directed to a single detector D.

Next, a method for measuring the absolute reflectance and the absolute transmittance for the face side incidence and the back side incidence on the sample T by an optical system for measurement of optical constant having the above configuration will be described below.

Firstly, a method for measuring the absolute reflectance will be described with the absolute reflectance from the sample face side determined by using the ellipsoidal mirrors EM1, EM4 and EM3 being defined as r, and with the absolute reflectance from the sample back side determined by using the ellipsoidal mirrors EM2, EM4 and EM3 being defined as r'.

In the measurement of the absolute reflectance from the face side, the light from the light source LS such as a spectrophotometer is received by the beam switching mirror RM1 held in the direction in FIG. 1, and transmitted to the ellipsoidal mirror EM1. The ellipsoidal mirror EM1 converges this light at the sample holder SH. For measuring the background signal, the through hole B is selected in the sample holder SH, and all the light is transmitted to the ellipsoidal mirror EM4 (indicated by a dotted line). The ellipsoidal mirror EM4 converges this light and transmits it to the beam switching mirror RM2, and the light is converged in a detector D such as a spectrophotometer. The output in this state is defined to be $I_0$.

Next, in order to measure the sample signal reflected from the sample T, the sample T is selected in the sample holder SH, and the incoming light is reflected by the sample T (indicated by a solid line) and transmitted to the ellipsoidal mirror EM3. The ellipsoidal mirror EM3 converges this light and transmits it to the beam switching mirror RM2 turned to the ellipsoidal mirror EM3 side, and the light is converged on the detector D. The output in this state is defined to be $I_r$. The absolute reflectance r from the face side is determined as $r = I_r/I_0$.

In measuring the absolute reflectance from the sample back side, the light from the light source LS is received by the beam switching mirror RM1 turned to the ellipsoidal mirror EM2 side, and transmitted to the ellipsoidal mirror EM2. The ellipsoidal mirror EM2 converges this light at the sample holder SH. In order to measure the background signal, the through hole B is selected in the sample holder SH, and all the light is transmitted to the ellipsoidal mirror EM3 thereby. The ellipsoidal mirror EM3 converges this light and transmits it to the beam switching mirror RM2, and the light is converged on the detector D. The output in this state is defined to be $I'_0$.

Next, in order to measure the sample signal of the sample, the sample is selected in the sample holder SH, and the incoming light is reflected by the sample and transmitted to the ellipsoidal mirror EM4. The ellipsoidal mirror EM4 converges this light and transmits it to the turned beam switching mirror RM2, and the light is converged on the detector D. The output in this state is defined to be $I'_r$. The absolute reflectance r' from the back side is determined as $r'=I'_r/I'_0$. In a general sample, the absolute reflectance from the face side is not equal to the absolute reflectance from the back side ($r \neq r'$).

Next, description will be made on the measurement of the absolute transmittance from the face side of the sample and the absolute transmittance from the back side thereof by using this optical system for measurement of optical constant. In the measurement of the absolute transmittance from the face side of the sample, the light from the light source LS is firstly received by the beam switching mirror RM1, and transmitted to the ellipsoidal mirror EM1. The ellipsoidal mirror EM1 converges this light at the sample holder SH. In order to measure the background signal, the through hole is selected in the sample holder SH, and all the light is transmitted to the ellipsoidal mirror EM4. The ellipsoidal mirror EM4 converges this light, and transmits it to the beam switching mirror RM2, and the light is converged on the detector D. The output in this state is defined to be $I_0$.

In the measurement of the sample signal transmitted through the sample T, by selecting the sample T in the sample holder SH, only the light transmitted through the sample T out of the incoming light is transmitted to the same ellipsoidal mirror EM4. The ellipsoidal mirror EM4 converges this light and transmits it to the beam switching mirror RM2, and the light is converged on the detector D. The output in this state is defined to be $I_r$. The absolute transmittance t from the face side is determined as $t=I_r/I_0$.

In the measurement of the absolute transmittance from the back side of the sample, the light from the light source LS is received by the beam switching mirror RM1 turned to the ellipsoidal mirror EM2 side, and transmitted to the ellipsoidal mirror EM2. The ellipsoidal mirror EM2 converges this light at the sample holder SH. In order to measure the background signal, the through hole B is selected in the sample holder SH, and all the light is transmitted to the ellipsoidal mirror EM3 thereby. The ellipsoidal mirror EM3 converges this light and transmits it to the turned beam switching mirror RM2, and the light is converged on the detector D. The output in this state is defined to be $I'_0$.

In order to measure the sample signal transmitted through the sample T, the sample T is selected in the sample holder SH, and the light transmitted through the sample T out of the incoming light is transmitted to the same ellipsoidal mirror EM3. The ellipsoidal mirror EMS converges this light, and transmits it to the beam switching mirror RM2, and the light is converged on the detector D. The output in this state is defined to be $I'_r$. The absolute transmittance t' from the back side is determined as $t'=I'_r/I'_0$. The absolute transmittance from the face side is equal to the absolute transmittance from the back side in an ideal sample (t=t').

The switching of the sample T and the through hole B by the slide member SL, and the switching of the direction of the beam switching mirrors RM1 and RM2 can be operated in an interlocking manner according to the object to be measured.

Next, a second embodiment of the present invention will be described with reference to FIGS. 2 to 6.

Figure 2:
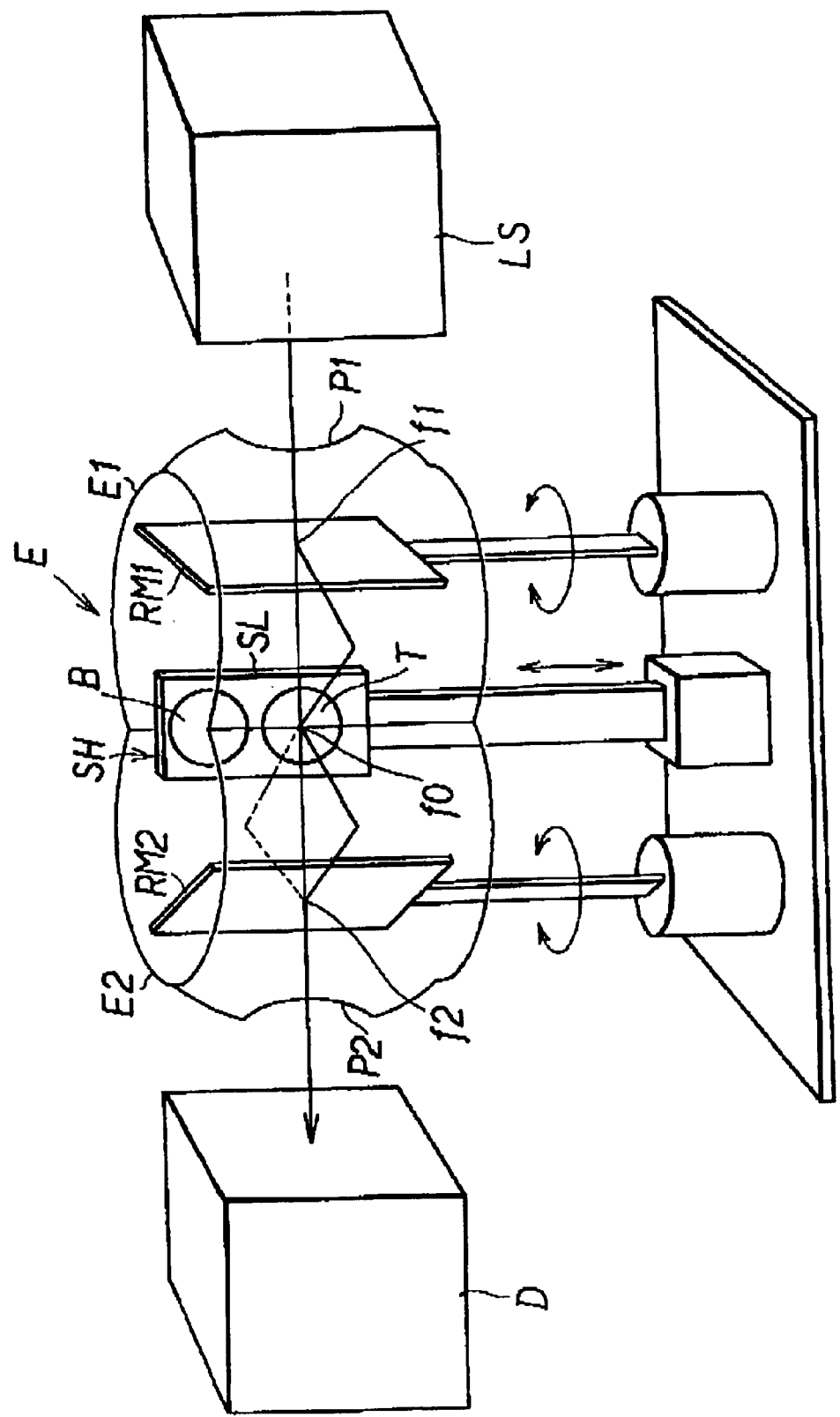
FIG. 2 is a perspective view showing the configuration according to a second embodiment of an optical system for measurement of optical constant in accordance with the present invention with the inside thereof in a perspective manner.

In this second embodiment, a bi-spheroidal mirror E comprising the first and second spheroidal mirrors E1 and E2 shown in FIG. 2 is used in place of the ellipsoidal mirrors EM1–EM4 used for converged light reflecting means and received light reflecting means in the first embodiment. Thus, an optical system of the second embodiment comprises the bi-spheroidal mirror E comprising the two spheroidal mirrors E1 and E2, two beam switching mirrors RM1 and RM2, and a sample holder SH.

In the bi-spheroidal mirror E, the two spheroidal mirrors E1 and E2 are disposed adjacent to each other so that the respective axes of rotation are on the same axis (on the optical axis connecting a light source to a detector which will be described below). These two spheroidal mirrors E1 and E2 are integrally coupled with each other at respective apertures thereof so that sections are agreed with each other if these spheroidal mirrors are cut in the plane orthogonal to the axis of rotation including focal points close to each other, and one focal point of both spheroidal mirrors E1 and E2 are agreed with each other as a common focal point f0. In addition, an incoming through hole P1 and an exiting through hole P2 are made in the incoming side of the first spheroidal mirror E1, and in the exiting side of the second spheroidal mirror E2, respectively.

When manufacturing the bi-spheroidal mirror E shown in the figure, two spheroidal mirrors E1 and E2 with insides thereof being mirror-finished are prepared first, and cut along the plane separated by the equal distance in the vertical direction from the horizontal plane including the axis connecting two focal points of these spheroids, and cut off along the plane perpendicular to the axis of rotation passing through one focal point of these spheroids. The respective focal points included in the cutting-off plane are agreed with each other to form the common focal point f0, and the two spheroidal mirrors E1 and E2 are disposed so that this common focal point f0 and two remaining focal points f1 and f2 are arranged on one line.

This line is agreed with the axis of rotation of the two spheroidal mirrors E1 and E2, and also forms the axis of rotation of the bi-spheroidal mirror E. Two through holes of the incoming through hole P1 and the exiting through hole P2 are formed along the axis at the intersections of this axis with the spheroidal mirrors E1 and E2 on both sides.

An external light source LS incident on the incoming through hole P1 is disposed on the axis, and a detector D for detecting the light exiting from the exiting through hole P2 is disposed on the axis. In addition, the sample holder SH is disposed at the common focal point f0, and the incoming side beam switching mirror RM1 and the exiting side beam switching mirror RM2 are disposed at the two remaining focal points f1 and f2 of the spheroidal mirror. The direction of these beam switching mirrors can be controlled, and thus, an optical arrangement for allowing the incidence at an arbitrary angle of incidence $\theta$ with respect to the sample can be determined thereby.

The sample holder SH substantially is not different from that in the first embodiment. Two holes of the same size are made in the slide member SL. One of them is a through hole B having no sample, and the other is a sample insertion hole capable of fitting the sample T, and the switching with or without the sample becomes possible. The beam switching mirrors RM1 and RM2 can also be operated in an interlocking manner by an interlocking mechanism (not shown) when switching this slide member. As a result, the detector D or mirrors need not be moved, the conventionally required "replacement" becomes unnecessary, the reproducibility of the spectra on the absolute reflectance and the absolute transmittance is also improved, and measurement errors can be reduced.

Next, the operation of the second embodiment will be described.

Practically speaking, in FIG. 2, the light is incident in this bi-spheroidal mirror E from the light source LS of the external light source and the spectrophotometer through the incoming side through hole P1. This incoming light is converged first in the beam switching mirror RM1, and the light reflected by this beam switching mirror RM1 reaches the spheroidal mirror E1 and is reflected thereby, and converged again on the sample T of the common focal point f0. A sample surface of the sample holder SH is set parallel to the axis of the bi-spheroidal mirror E. The light reflected by or transmitted through this sample surface reaches the spheroidal mirror E2 and is reflected thereby, and again, converged on the beam switching mirror RM2. The light reflected by the beam switching mirror RM2 passes on the optical axis of the original light source LS, and reaches the detector D. This arrangement is free from any chromatic aberration attributable to presence of mirrors, and capable of performing the measurement of high accuracy.

This optical system can measure the absolute reflectance and the absolute transmittance at an arbitrary angle of incidence with respect to the sample, and the measurement thereof will be described below with reference to FIGS. 3 to 6.

Firstly, the reflectance from the face side determined by the combination of a proximal surface of the spheroidal mirror E1 and the spheroidal mirror E2 is defined as r, and the reflectance from the back side determined by the combination of a distal surface of the spheroidal mirror E1 with the spheroidal mirror E2 is defined as r'.

In addition, the angle at which the beam switching mirror RM1 is directed in the direction of the light source LS and perpendicular to the axis of rotation of the bi-spheroidal mirror E is defined to be zero. On the other hand, the angle at which the beam switching mirror RM2 is directed in the direction of the detector D and perpendicular to the axis of rotation thereof is defined to be zero.

Figure 3:
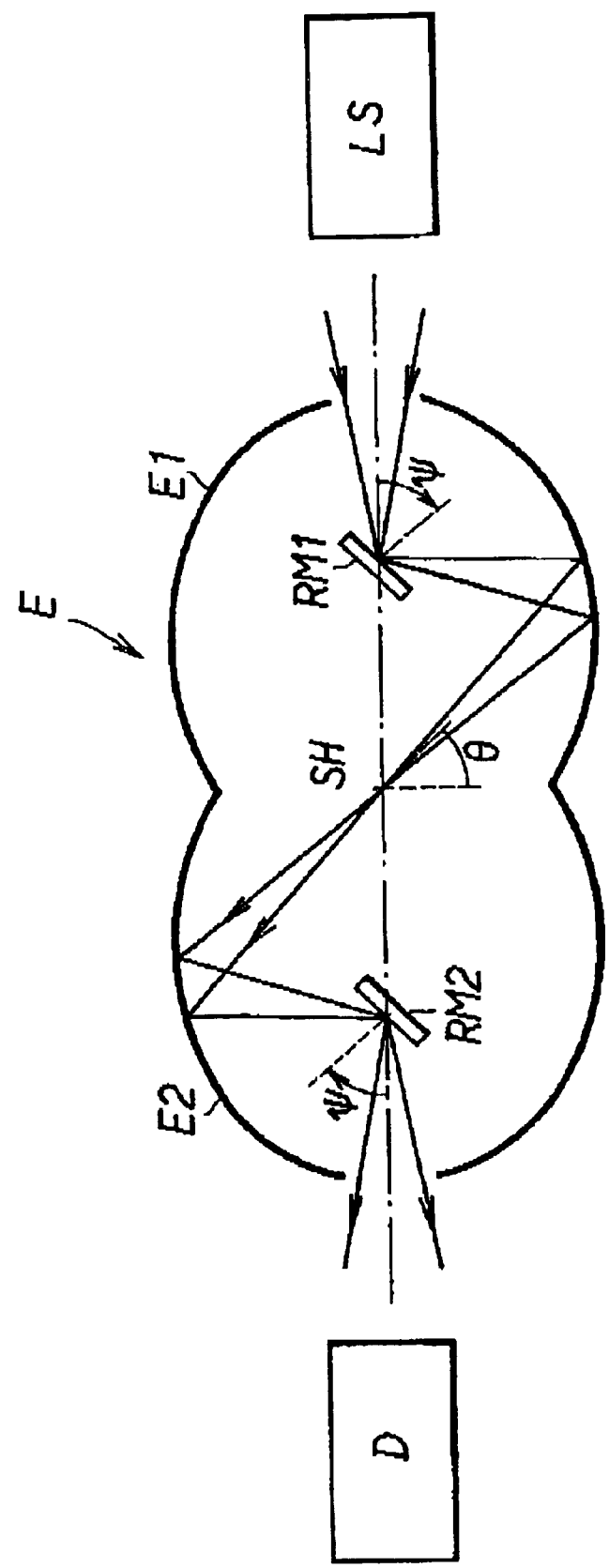
FIG. 3 is a schematic representation of the measurement of background for face side incidence according to the second embodiment.
Figure 4:
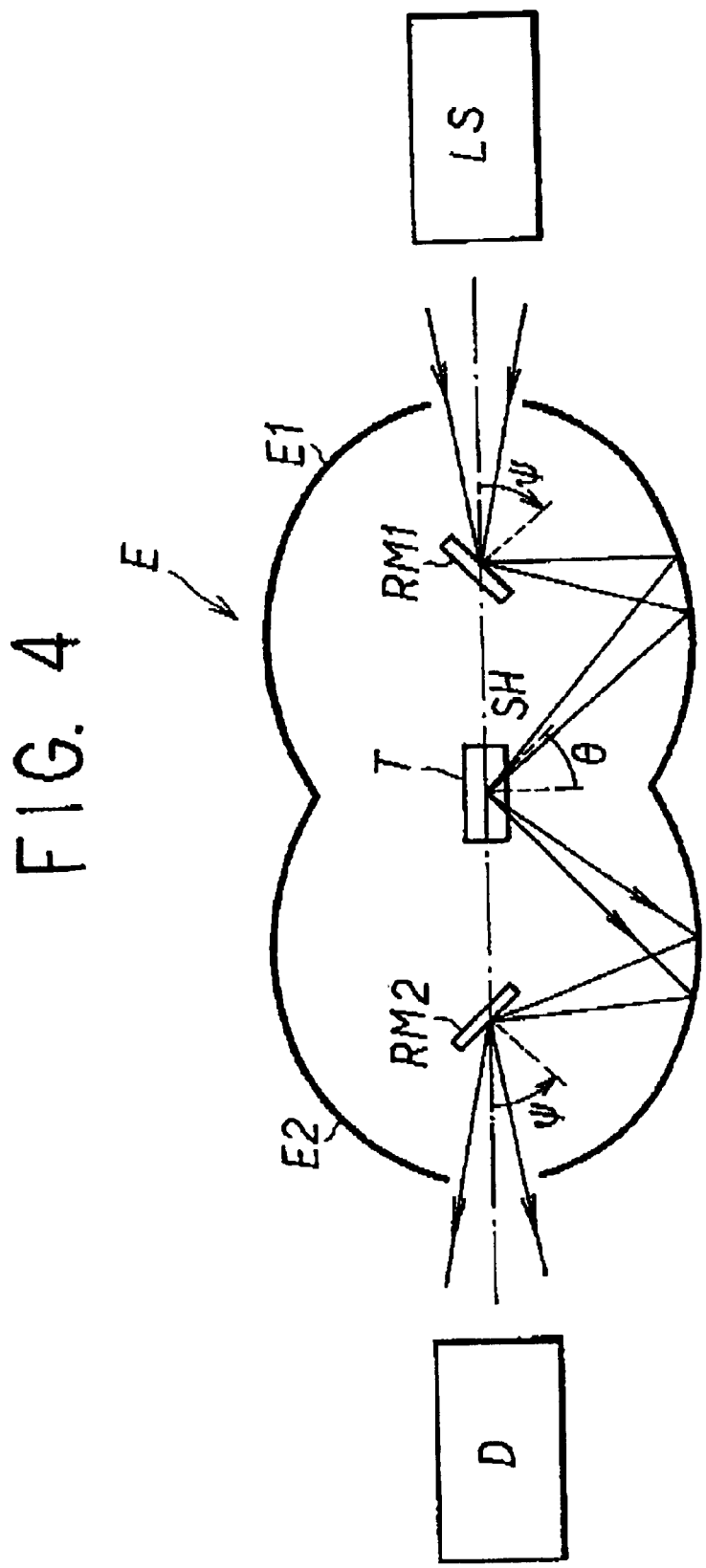
FIG. 4 is a schematic representation of the measurement of sample reflection for face side incidence according to the second embodiment.

The measurement of the reflectance from the face side of the sample will be described. In FIGS. 3 and 4, the optical axis of the light incoming from the light source LS in the bi-spheroidal mirror E is assumed coincident with the axis of rotation of the bi-spheroidal mirror E. In this case, the angle at which the incoming light reflected by the beam switching mirror RM1 by appropriately turning the beam switching mirror RM1 clockwise is projected on the face side in the proximal side of the spheroidal mirror E1 in FIG. 3 (hereinafter, referred to as "a front surface") is defined as $\psi$ (degree). In this state, the light reflected by the spheroidal mirror E1 is incident from the face side of the sample holder SH at the angle of incidence of θ degrees.

In order to measure the background signal, the through hole B is selected in the sample holder SH, and the incoming light passes through the through hole B in the sample holder SH as shown in FIG. 3, and is reflected by the spheroidal surface on the distal side of the spheroidal mirror E2 in FIG. 3 (hereinafter, referred to as "back surface"), and converged to the beam switching mirror RM2. In this state, the reflected light of the beam switching mirror RM2 by turning the beam switching mirror RM2 clockwise by $\psi$ degrees is allowed coincident with the optical axis of the original external light source LS. Thus, the light is converged on the detector D. The output in this state is defined as $I_0$.

Next, in order to measure the sample signal of the sample, if the sample T is selected in the sample holder SH, the incoming light is reflected by the sample, reflected by the front surface of the spheroidal mirror E2, and converged on the beam switching mirror RM2. The reflected light of the beam switching mirror RM2 by turning the beam switching mirror RM2 counterclockwise by substantially Y degrees is allowed coincident with the optical axis of the original external light source, and the light is converged on the detector D thereby. In this state, the output is defined as $I_r$. The reflectance r from the face side of the sample is determined as $r=I_r/I_0$.

Figure 5:
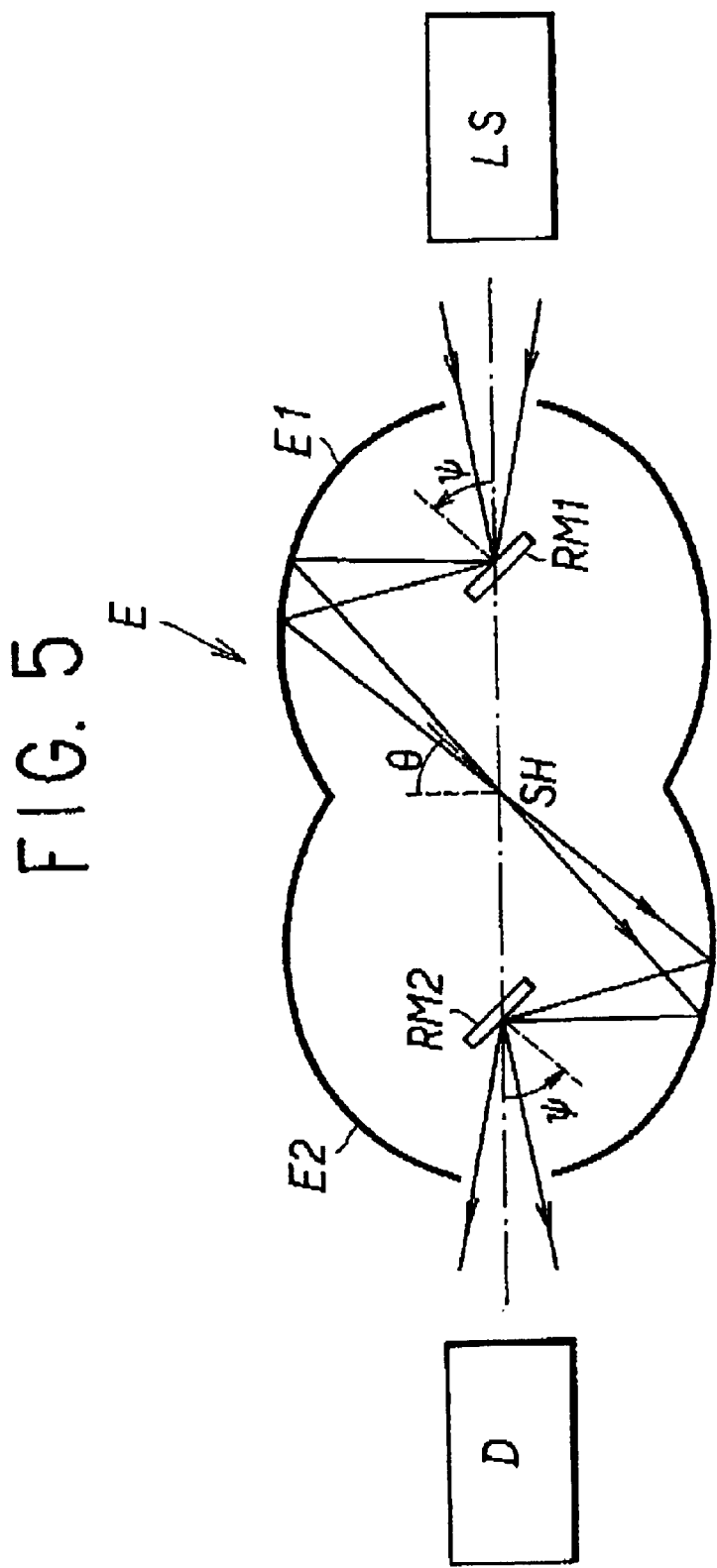
FIG. 5 is a schematic representation of the measurement of background for back side incidence according to the second embodiment.
Figure 6:
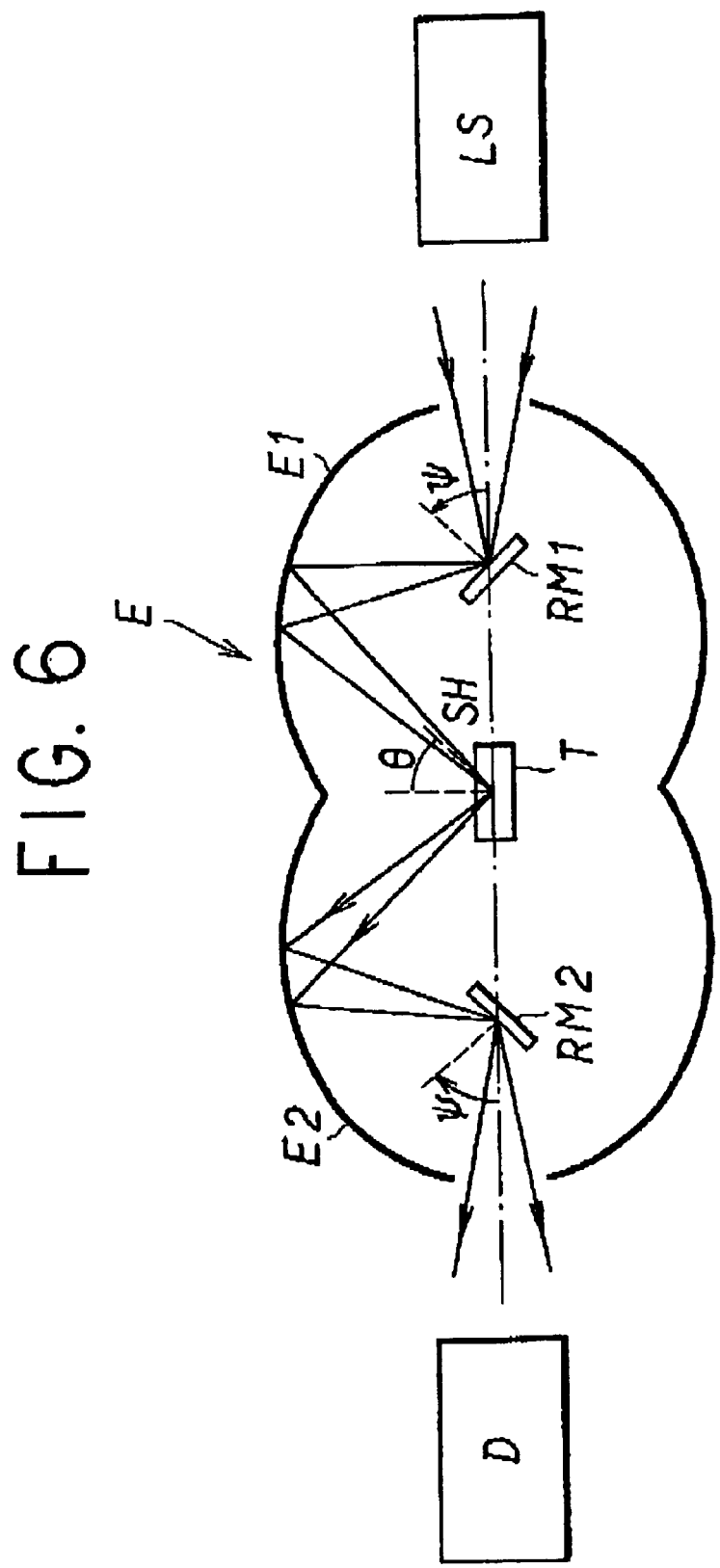
FIG. 6 is a schematic representation of the measurement of sample reflection for back side incidence in the second embodiment.

In the measurement of the reflectance from the back side of the sample, the angle at which the light from light source LS is received by the beam switching mirror RM1 turned counterclockwise in FIGS. 5 and 6, and the incoming light reflected by the beam switching mirror RM1 is projected on the back surface of the spheroidal mirror E1 is defined as $\psi$ degrees (FIG. 5). In this state, the light reflected by the spheroidal surface is incident from the back side of the sample holder SH at the angle of incidence θ.

In order to measure the background signal, the through hole B is selected in the sample holder SH, and the light passes through the through hole in the sample holder SH as shown in FIG. 5, and is reflected by the front surface of the spheroidal mirror E2, and converged on the beam switching mirror RM2. In this state, the reflected light of the beam switching mirror RM2 by turning the beam switching mirror RM2 counterclockwise by Y degrees is allowed coincident with the optical axis of the original external light source. Thus, the light is converged on the detector D. The output in this state is defined as $I'_0$.

Next, in order to measure the sample signal of the sample, the sample T is selected in the sample holder SH, and the incoming light is reflected by the sample T as shown in FIG. 6, reflected by the back surface of the spheroidal mirror E2, and converged on the beam switching mirror RM2. In this state, the reflected light of the beam switching mirror RM2 by turning the beam switching mirror RM2 clockwise by substantially Y degrees is allowed coincident with the optical axis of the original external light source. Thus, the light is converged on the detector D. The output in this state is defined as $I'_r$. The reflectance r' from the back side of the sample is determined as $r'=I'_r/I'_0$. Generally speaking, even with a bulk sample having both sides being mirror-polished, the reflectance from the face side is not equal to the reflectance from the back side (r≠r').

Next, description will be made on the measurement of the absolute transmittance from the face side and the absolute transmittance from the back side of a transparent sample by using this optical system.

Firstly, when measuring the absolute transmittance from the face side of the sample by combining the front surface of the spheroidal mirror E1 with the back surface of the spheroidal mirror E2, the light from the light source LS is received by the beam switching mirror RM1 in FIG. 3, and the incoming light reflected by the beam switching mirror RM1 by appropriately turning the beam switching mirror RM1 clockwise is projected on the front surface of the spheroidal mirror E1, and the angle in this state is defined as ψ degrees. The light reflected by the spheroidal surface E1 is incident from the face side of the sample holder SH at the angle of incidence θ.

In order to measure the background signal, the through hole B is selected in the sample holder SH, the light passes through the through hole B of the sample holder SH as shown in FIG. 3, and is reflected by the back surface of the spheroidal mirror E2, and converged by the beam switching mirror RM2. In this state, the reflected light of the beam switching mirror RM2 by turning the beam switching mirror RM2 clockwise by ψ degrees is allowed coincident with the optical axis of the original external light source LS. Thus, the light is converged on the detector D. The output in this state is defined as $I_0$.

Next, in order to measure the sample signal of the sample, the sample T is selected in the sample holder SH, and the light transmitted through the sample T out of the incoming light in FIG. 3 is reflected by the back surface of the spheroidal mirror E2, and converged on the beam switching mirror RM2. In this state, the reflected light of the beam switching mirror RM2 by turning the beam switching mirror RM2 clockwise by substantially ψ degrees is allowed coincident with the optical axis of the original external light source. The light is converged on the detector D thereby. The output in this state is defined as $I_t$, and the absolute transmittance t from the face side is determined as $t=I_t/I_0$.

When measuring the absolute transmittance from the back side of the sample by combining the back surface of the spheroidal mirror E1 with the front surface of the spheroidal mirror E2, the light from the light source LS is received by the beam switching mirror RM1 turned counterclockwise as shown in FIG. 5, and the incoming light reflected by the beam switching mirror RM1 is projected on the back surface of the spheroidal mirror E1. The angle of the beam switching mirror RM1 in this state is defined as ψ degrees, and the light reflected by the spheroidal surface is allowed to be incident from the back side of the sample holder SH at the angle of incidence θ.

In order to measure the background signal, the through hole B is selected in the sample holder SH, and the light passes through the through hole B in the sample holder SH, and is reflected by the front surface of the spheroidal mirror E2, and converged on the beam switching mirror RM2. In this state, the reflected light of the beam switching mirror RM2 by turning the beam switching mirror RM2 counterclockwise by ψ degrees is allowed to be coincident with the optical axis of the original external light source. Thus, the light is converged on the detector D. The output in this state is defined as $I'_0$.

In order to measure the sample signal of the sample, the sample T is selected in the sample holder SH, and the light transmitted through the sample out of the incoming light in FIG. 5 is reflected by the front surface of the spheroidal mirror E2, and converged on the beam switching mirror RM2. In this state, the reflected light of the beam switching mirror RM2 by turning the beam switching mirror RM2 counterclockwise by substantially ψ degrees is allowed to be coincident with the optical axis of the original external light source LS. Thus, the light is converged on the detector D. The output in this state is defined as $I'_t$, the absolute transmittance t' from the back side of the sample can be determined as $t'=I'_t/I'_0$. The absolute transmittance from the face side is equal to the absolute transmittance from the back side in an ideal sample (t=t').

In the optical system of the second embodiment using this bi-spheroidal mirror E, the angle ψ f the incoming light on the beam switching mirror RM1 can be changed in a range of projection on the spheroidal mirror E1, the angle of incidence θ on the sample can also be changed, and the angle of incidence can thus be continuously and arbitrarily changed from about 1 degree to about 89 degrees. By using this optical system, in a transparent substance such as dielectric, both the absolute reflectance and the absolute transmittance are measured at a predetermined angle of incidence, and these simultaneous equations including two unknowns of the refractive index and the attenuation coefficient (optical constants) are solved to determine the optical constants with excellent accuracy.

In addition, the absolute reflectance can be measured at an arbitrary angle of incidence, and for non-transparent samples such as metal, the absolute reflectance is measured at two different angles of incidence, and simultaneous equations including two unknowns of the refractive index and the attenuation coefficient (optical constants) are solved to determine the optical constants with excellent accuracy. In this state, in order to improve the measurement accuracy, the difference between these two angles of incidence is preferably made as large as possible. For this purpose, two sets of reflectance are preferably measured in substantially perpendicular incidence (within 10°) and grazing incidence (not less than 80°).

Further, in this optical system, the light scattering by the sample can also be measured by fixing the beam switching mirror RM1 and changing the above angle ψ of the beam switching mirror RM2.

In addition, this optical system is capable of continuously changing the angle of incidence of the sample, and measuring the spectrum not affected by the multiple reflection inside a substrate in a composite sample such as a thin film on the substrate. As a result, the optical constant of the thin film can be determined with excellent accuracy.

This means that, in the sample of the thin film on the substrate, a fringe generally appears in the reflection spectrum and the transmission spectrum due to the multiple reflection within the substrate. This fringe causes degradation of the accuracy when measuring the optical characteristic of the thin film with high accuracy. For the spectrum measurement without this fringe, any multiple reflection must be prevented within the substrate, and it can be remedied by allowing the P-polarized light to be incident on the sample at the Brewster's angle of the substrate. Since this Brewster's angle is a function of the wavelength, and the angle must be changed every time when the wavelength is changed. However, this optical system can easily perform this operation, and as a result, the optical constant of the thin film can be determined with excellent accuracy.

In the second embodiment, the S-polarized light and the P-polarized light are incident on a thin film sample, etc. on the substrate for the sample T of the sample holder SH while changing the angle of incidence, the polarized state of the reflected light is measured, an appropriate reference sample, for example, the substrate is fitted in the through hole B, the S-polarized light and the P-polarized light are allowed to be incident on the substrate while changing the angle of incidence, the polarized state of the reflected light is measured, and information on the optical constant of the thin film is determined from the difference of these two polarized states.

In addition, when a transparent substance having the refractive index larger than that of the sample is closely affixed to the sample, and held by the sample holder SH, and the light is allowed to be incident from the substance side thereon while changing the angle of incidence, attenuation of the reflective light occurs based on the absorption of the sample when the angle of incidence is larger than the angle for total reflection. On the other hand, when the reflective light is measured while changing the angle of incidence by holding this substance as the reference sample in the through hole B of the sample holder SH, the optical information, etc. in the depth direction of the sample can be determined from the difference between these two sets of reflectance.

Figure 7:
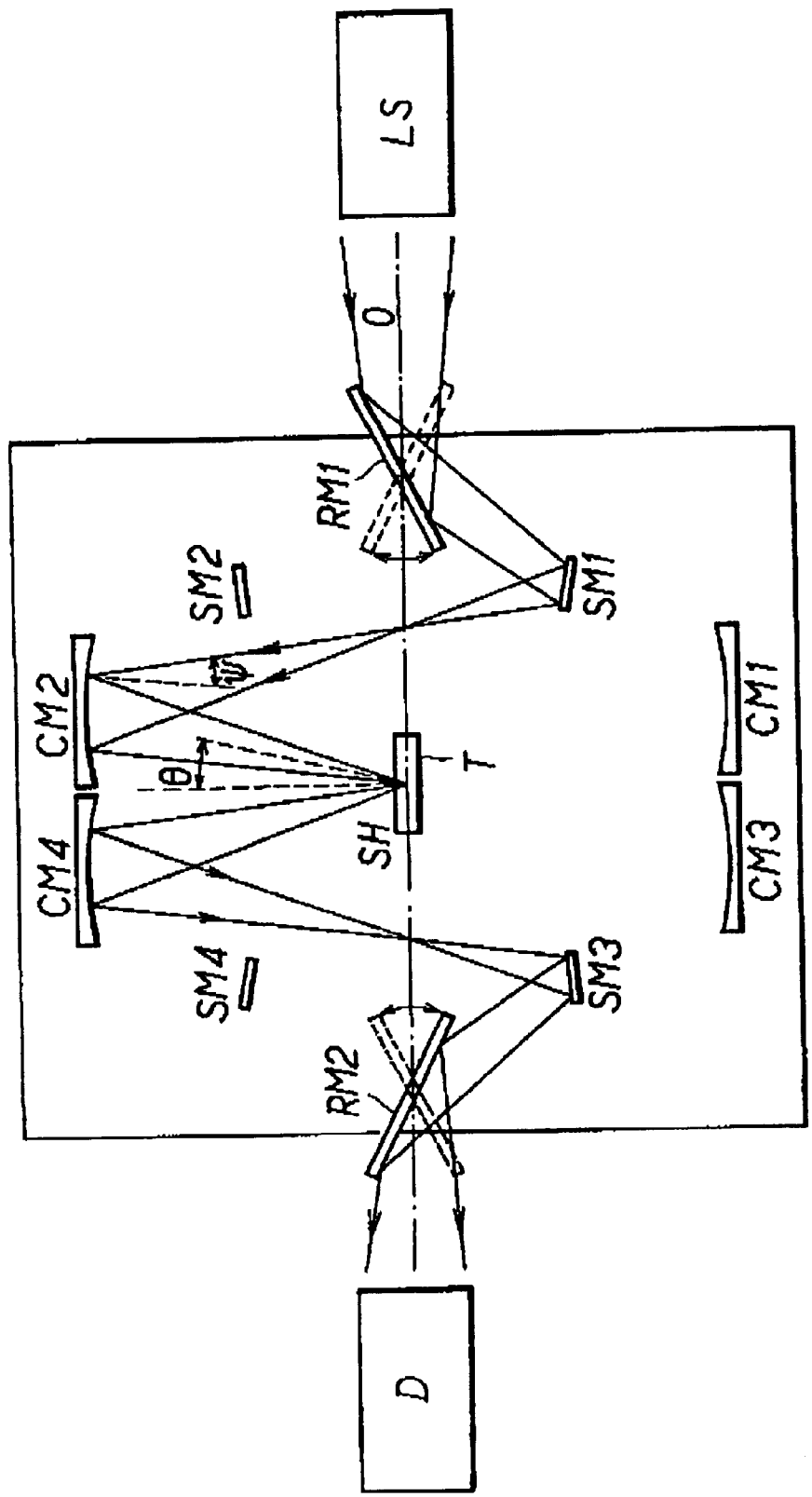
FIG. 7 is a plan view schematically showing the configuration according to a third embodiment of an optical system for measurement of optical constant in accordance with the present invention.

FIG. 7 shows a third embodiment of the optical system for measurement of optical constant in accordance with the present invention. This third embodiment shows the configuration of the optical system for measurement of optical constant when the focal point in the system comprising the external light source LS (for example, laser and microwave) and the detector D, or the optical system of a dispersion type spectrophotometer or a Fourier transformation type spectrophotometer is not coincident with the beam switching mirrors RM1 and RM2.

This optical system for measurement of optical constant comprises two beam switching mirrors RM1 and RM2, four concave mirrors CM1, CM2, CM3 and CM4, four supplementary mirrors SM1, SM2, SM3 and SM4, and the sample holder SH. The converged light reflecting means and the received light reflecting means are constituted by combining the concave mirrors with the supplementary mirrors.

The configuration of the third embodiment will be described below more specifically. This embodiment has an optical arrangement in which the light is allowed to be incident on the sample at an arbitrary angle of incidence θ, and the sample holder SH is disposed at the position of the original focal point of the dispersion type or Fourier transformation type spectrophotometer. Two beam switching mirrors RM1 and RM2, and the sample holder SH are disposed in one row on the axis connecting the incoming side of this optical system to the exiting side thereof (the original optical axis O), and the beam switching mirror RM1 and the beam switching mirror RM2 are disposed on the incoming side and the exiting side, respectively, with the sample holder SH thereacross.

Four concave mirrors CM1–CM4 are disposed in an X-shape symmetry to the sample holder SH at the center, and disposed at equal distance (the distance as large as or slightly smaller than the radius of curvature of the concave mirrors) so that the light is allowed to be incident on the sample at the equal angle of incidence θ from the face and back sides, and exit therefrom at the equal angle of incidence θ.

The direction of the four concave mirrors CM1–CM4 is determined so that the angle ψ of incidence to each concave mirror becomes smaller. The four supplementary mirrors SM1–SM4 are disposed by adjusting the position of the supplementary mirrors so that the focal points after the light is reflected by the beam switching mirrors RM1 and RM2 and the supplementary mirrors SM1–SM4 are on the original optical axis of the dispersion type or Fourier transformation type spectrophotometer, and the angle of incidence on the concave mirrors is substantially ψ.

In this disposition, the light incident on the beam switching mirror RM1 of the optical system for measurement of optical constant is converged once on the original optical axis O, and then, converged on the sample surface again by the concave mirror CM2 or CM1. The light reflected by or transmitted through the sample surface is converted again on the original optical axis O by the concave mirror CM3 or CM4, reflected by the beam switching mirror RM2, and passes on the optical axis O of the original dispersion type or Fourier transformation type spectrophotometer. As a result, in this disposition, the chromatic aberration by the mirrors becomes small, and the measurement of high accuracy can be performed not only by the ellipsoidal mirrors but also by the concave mirrors CM1–CM4.

The sample holder SH has the substantially same configuration as that in the first or second embodiment. It can also be operated in an interlocking manner with the beam switching mirrors RM1 and RM2.

In the optical system for measurement of optical constant according to the third embodiment having the above configuration, the absolute reflectance of the sample to the face side incidence and the back side incidence can be measured as follows.

Firstly, the absolute reflectance from the face side determined by the combination of the concave mirrors CM1, CM4 and CM3 is defined as r, and the absolute reflectance from the back side by the combination of the concave mirrors CM2, CM3 and CM4 is defined as r'.

In the measurement of the absolute reflectance from the face side of the sample, the light from the light source LS of the spectrophotometer, etc. is received by the beam switching mirror RM1, transmitted to the supplementary mirror SM2, and further transmitted to the concave mirror CM1. The concave mirror CM1 converges this light at the sample holder SH. In order to measure the background signal, the through hole B is selected in the sample holder SH, all the light is converged by the concave mirror CM4, transmitted to the supplementary mirror SM3, and further transmitted to the beam switching mirror RM2 to allow the reflected light of the beam switching mirror RM2 to be coincident with the original optical axis O of the spectrophotometer. Thus, the light is converged on the detector D. The output in this state is defined as $I_0$.

Next, in order to measure the sample signal of the sample, the sample T is selected in the sample holder SH, the incoming light is reflected by the sample T, and transmitted to the concave mirror CM3. The concave mirror CM3 converges this light, transmits it to the supplementary mirror SM4, further transmits it to the torned beam switching mirror RM2, and allows the reflected light of the beam switching mirror RM2 to be coincident with the original optical axis O of the spectrophotometer. Thus, the light is converged on the detector. The output in this state is defined as $I_r$. The absolute reflectance from the face side of the sample is determined as $r=I_r/I_0$.

Next, description will be made on the measurement of the absolute reflectance from the back side of the sample. The light from the light source LS of the spectrophotometer, etc. is received by the turned beam switching mirror RM1, transmitted to the supplementary mirror SM1, and further transmitted to the concave mirror CM2. The concave mirror CM2 converges this light at the sample holder SH. In order to measure the background signal, the through hole B is selected in the sample holder SH, all the light is converged by the concave mirror CM3, transmitted to the supplementary mirror SM4, further transmitted to the beam switching mirror RM2 to allow the reflected light of the beam switching mirror RM2 to be coincident with the original optical axis O of the spectrophotometer. Thus, the light is converged on the detector D. The output in this state is defined as $I'_0$.

In order to measure the sample signal of the sample, the sample T is selected in the sample holder SH, and the incoming light is reflected by the sample T, and transmitted to the concave mirror CM4. The concave mirror CM4 converges this light, transmits it to the supplementary mirror SM3, further transmits it to the torned beam switching mirror RM2, and allows the reflected light of the beam switching mirror RM2 to be coincident with the original optical axis O of the spectrophotometer. Thus, the light is converged on the detector D. The output in this state is defined as $I'_r$. The absolute reflectance r' from the back side of the sample is determined as $r'=I'_r/I'_0$. Generally speaking, even with a bulk sample having both sides being mirror-polished, the absolute reflectance from the face side is not equal to the absolute reflectance from the back side (r≠r').

Next, description will be made on the measurement of the absolute transmittance from the face side of the transparent sample and the absolute transmittance from the back side thereof by using this optical system for measurement of optical constant.

Firstly, the light intensity is measured at the through hole B and the sample T, respectively, by using the concave mirror CM1 and the concave mirror CM4, and the absolute transmittance t from the face side is determined from the ratio thereof.

More specifically, the light from the light source LS of the spectrophotometer, etc. is received by the beam switching mirror RM1, transmitted to the supplementary mirror SM2, and further transmitted to the concave mirror CM1. The concave mirror CM1 converges this light at the sample holder SH. In order to measure the background signal, the through hole B is selected in the sample holder SH, all the light is converged by the concave mirror CM4, transmitted to the supplementary mirror SM3, further transmitted to the beam switching mirror RM2 to allow the reflected light of the beam switching mirror RM2 to be coincident with the original optical axis O of the spectrophotometer. Thus, the light is converged on the detector. The output in this state is defined as $I_0$.

Next, in order to measure the sample signal of the sample, the sample T is selected in the sample holder SH, the light transmitted through the sample T out of the incoming light is converged by the same concave mirror CM4, transmitted to the supplementary mirror SM3, further transmitted to the beam switching mirror RM2 to allow the reflected light of the beam switching mirror RM2 to be coincident with the original optical axis O of the spectrophotometer. Thus, the light is converged on the detector D). The output in this state is defined as $I_r$. The absolute transmittance t from the face side of the sample can be determined as $t=I_r/I_0$.

Next, the light intensity of the through hole and the sample is measured respectively by using the concave mirror CM2 and the concave mirror CM3, and the absolute transmittance t' from the back side is determined from the ratio thereof.

More specifically, the light from the light source LS of the spectrophotometer, etc. is received by the beam switching mirror RM1, transmitted to the supplementary mirror SM1, and further transmitted to the concave mirror CM2. The concave mirror CM2 converges this light at the sample holder SH. In order to measure the background signal, the through hole B is selected in the sample holder SH, all the light is converged by the concave mirror CM3, transmitted to supplementary mirror SM4, further transmitted to the beam switching mirror RM2 to allow the reflected light of the beam switching mirror RM2 to be coincident with the original optical axis O of the spectrophotometer. Thus, the light is converged on the detector. The output in this state is defined as $I'_0$.

Next, in order to measure the sample signal of the sample, the sample T is selected in the sample holder SH, and the light transmitted through the sample out of the incoming light is converged by the same concave mirror CM3, transmitted to the supplementary mirror SM4, further transmitted to the beam switching mirror RM2 to allow the reflected light of the beam switching mirror RM2 to be coincident with the original optical axis O of the spectrophotometer. Thus, the light is converged on the detector D. The output in this state is defined as $I'_r$. The absolute transmittance t' from the back side of the sample can be determined as $t'=I'_r/I'_0$. The absolute transmittance from the face side is equal to the absolute transmittance from the back side in an ideal sample (t=t').

Figure 8:
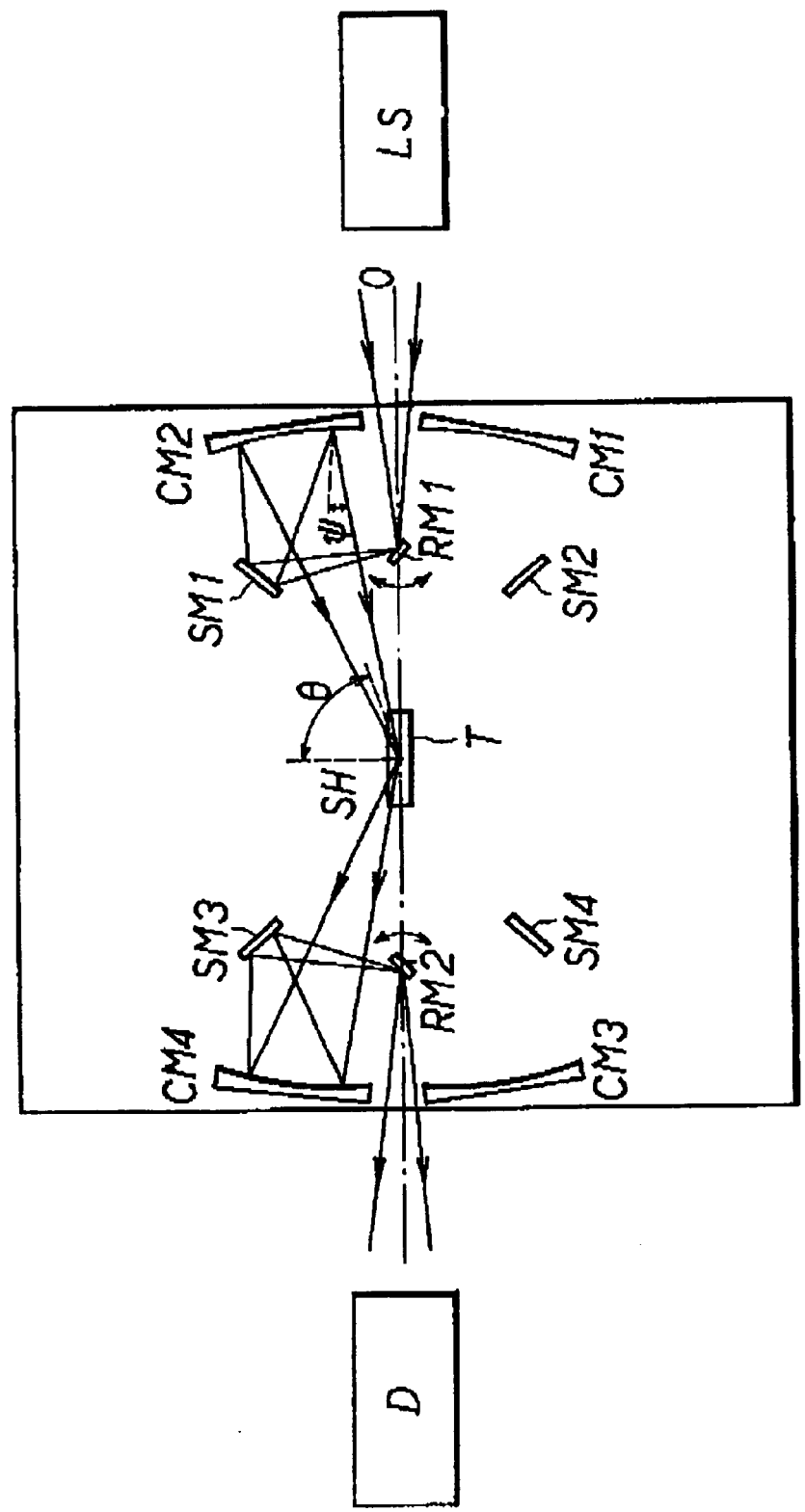
FIG. 8 is a plan view schematically showing the configuration according to a fourth embodiment of an optical system for measurement of optical constant in accordance with the present invention.

FIG. 8 shows a fourth embodiment of the optical system for measurement of optical constant in accordance with the present invention.

This fourth embodiment indicates the configuration of the optical system in which the focal point by the system comprising an external light source LS (for example, laser and microwave) and a detector D, or by the optical system of the dispersion type spectrophotometer or the Fourier transformation type spectrophotometer is coincident with each beam switching mirror, and the basic configuration thereof is the substantially same as that of the third embodiment in that this optical system comprises two beam switching mirrors RM1 and RM2, four concave mirrors CM1, CM2, CM3 and CM4, four supplementary mirrors SM1, SM2, SM3 and SM4, and the sample holder SH, but this optical system is different from the third embodiment in that the light is converted on the beam switching mirror RM1 and the beam switching mirror RM2.

More specifically, in this fourth embodiment, four concave mirrors CM1–CM4 are disposed in an X-shape symmetry at equal distance (the distance as large as or slightly smaller than the radius of curvature of the concave mirrors) at the equal angle of incidence θ with respect to the sample holder SH. In addition, the direction of the four concave mirrors CM1–CM4 is determined so that the angle ψ of incidence to each concave mirror becomes smaller. The light from the light source LS of the dispersion type or Fourier transformation type spectrophotometer, etc. is converged first on the first beam switching mirror RM1.

The supplementary mirror SM2 is disposed so that the optical path length from the beam switching mirror RM1 to the supplementary mirror CM1 via the concave mirror SM2 is equal to the optical path length from the concave mirror CM1 to the sample holder SH, and the angle of incidence with respect to the concave mirrors is substantially ψ. The remaining supplementary mirrors SM2, SM3 and SM4 are similarly disposed.

In this disposition, the light converged on the beam switching mirror RM1 first is again converged on the sample after passing through the supplementary mirrors SM2 or SM1, and the concave mirrors CM1 or CM2. The light reflected by or transmitted through the sample surface is converged after passing through the concave mirrors CM3 or CM4, and the supplementary mirror SM4 or SM3. The beam switching mirror RM2 is disposed on the position, and the light reflected by the beam switching mirror RM2 passes on the original optical axis O of the dispersion type or Fourier transformation type spectrophotometer. As a result, in this disposition, the chromatic aberration by the mirrors is reduced, and the measurement of high accuracy can be performed by not only the ellipsoidal mirrors but also the concave mirrors CM1–CM4.

The configuration of the sample holder SH is the substantially same as that of the above embodiments, and the operation in an interlocking manner with that of the beam switching mirrors RM1 and RM2 can be performed. In this disposition, both the absolute reflectance and the absolute transmittance can be measured by the same way mentioned in the third embodiment.

In each of the above embodiments, it is described that the light source LS may include laser, microwave source and the light sources in the dispersion type spectrophotometer and Fourier transformation type spectrophotometer.

Figure 9:
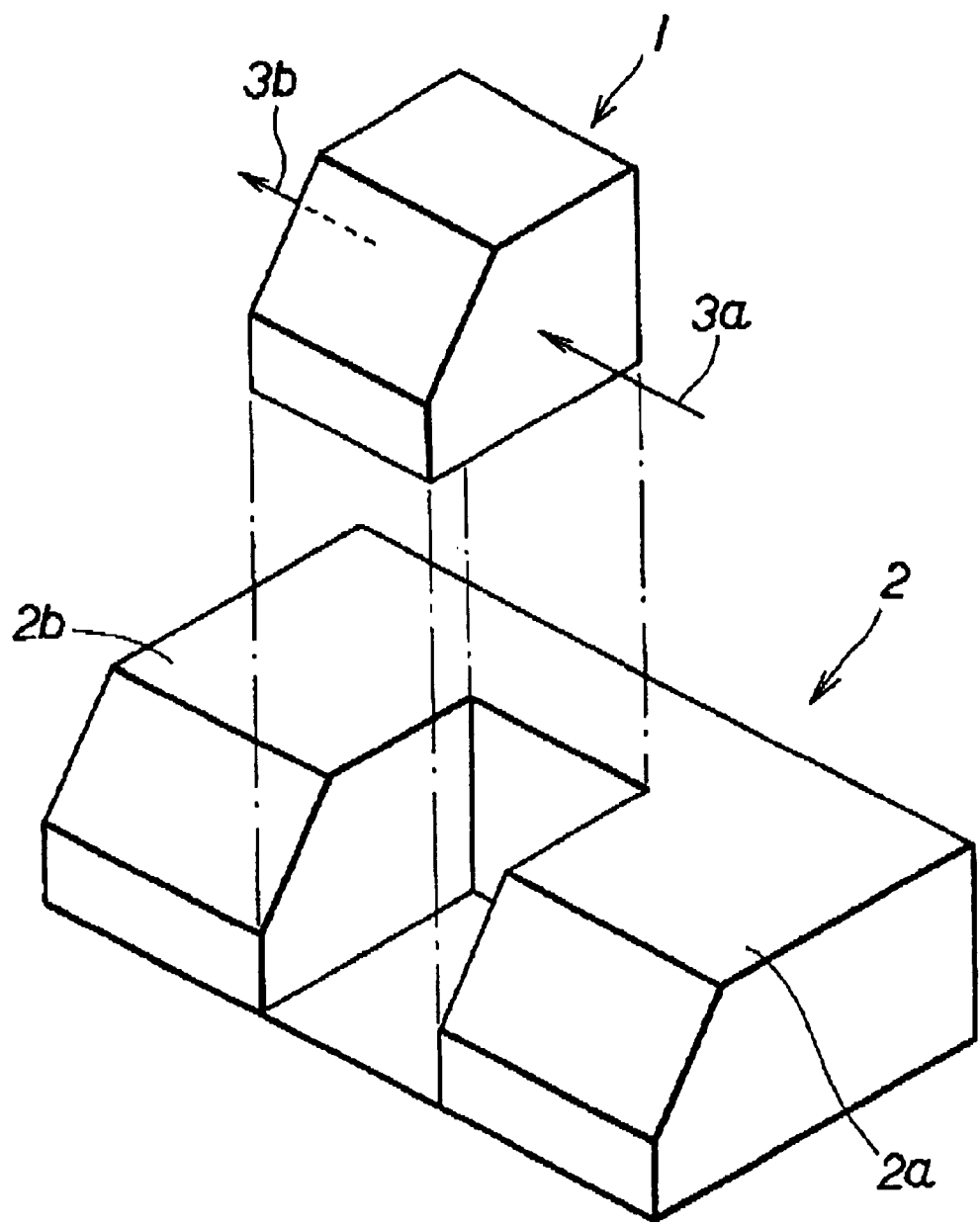
FIG. 9 is a perspective view of the assembly of an optical system in accordance with the present invention in a spectrophotometer.

FIG. 9 illustrates the form that the optical system 1 for measurement of optical constant of the above embodiments is built in the spectrophotometer 2. The optical system 1 for measurement of optical constant may be any one of those according to the above embodiments, and the spectrophotometer 2 may be any spectrophotometer on the market, or one designed for building in the optical system 1. The optical system 1 is fitted to the spectrophotometer 2 so that the optical axis of the incoming light 3a is aligned to the optical axis of a light source part 2a of the spectrophotometer 2, and the optical axis of the exiting light 3b is aligned to the optical axis of a detection unit 2b of the spectrophotometer 2.

The present invention is described with reference to the above embodiments. However, the present invention is not limited to these embodiments, and it goes without saying that the embodiments can be arbitrarily modified within the technical scope of the claims.

Next, the experimental examples according to the third embodiment will be described.

Figure 10:
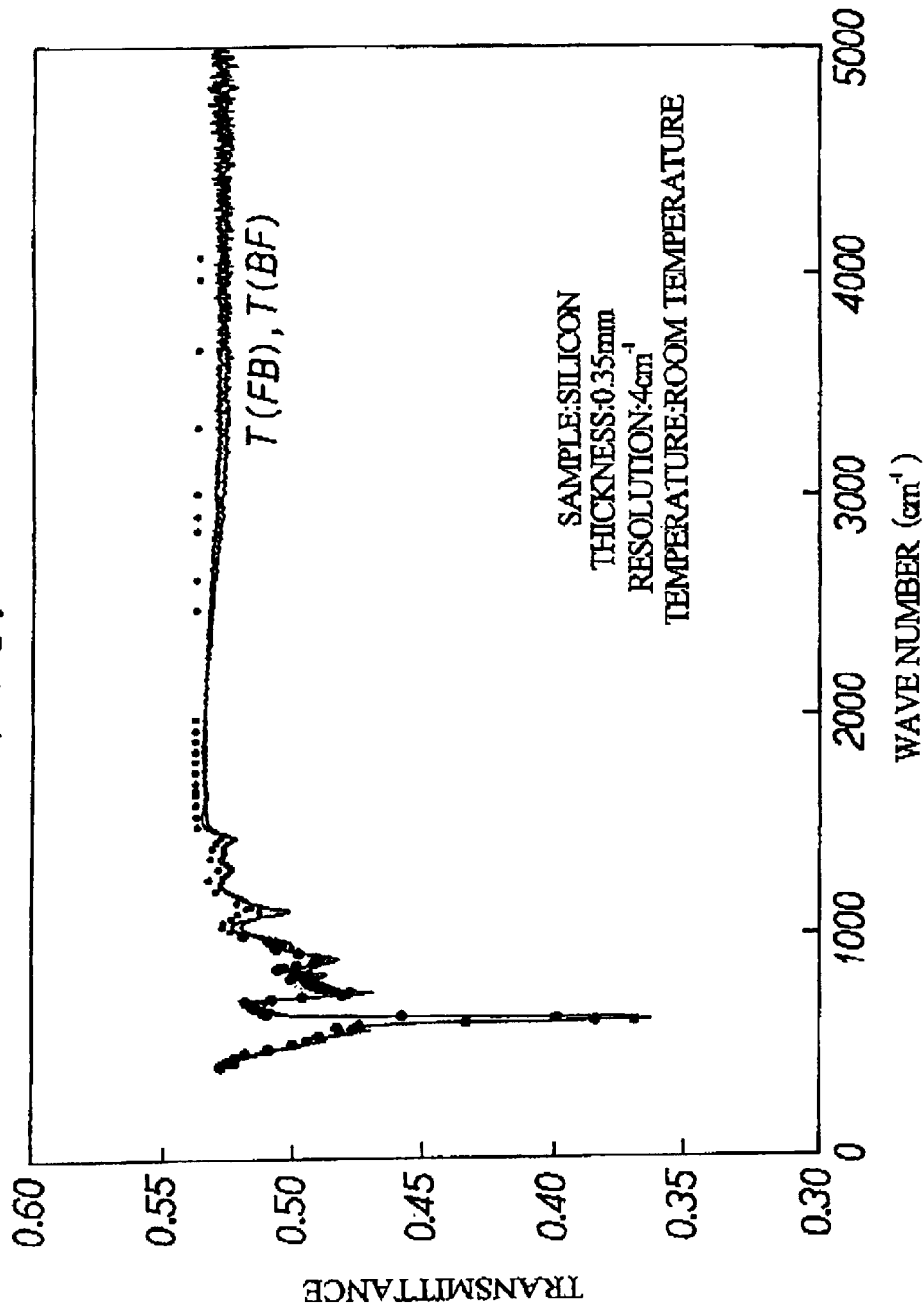
FIG. 10 is spectra showing the experimental result of the transmittance measurement of a pure silicon sample by an optical system in accordance with the present invention.

Result of Measurement:

FIG. 10 shows the result of measurement of transmittance of the pure silicon sample at room temperature. Two solid lines in the figure (almost overlapping) indicate the transmittance for the face side incidence and the back side incidence (T(FB) and T(BF)), respectively. The dots indicate the transmittance calculated from the data book. As a result, it can be understood that the transmittance can be measured within the measurement errors of ±0.4%. This excellent agreement indicates that combination of the same optical paths and the same mirrors is employed for the background signal and the sample signal in each measurement of the transmittance.

Figure 11:
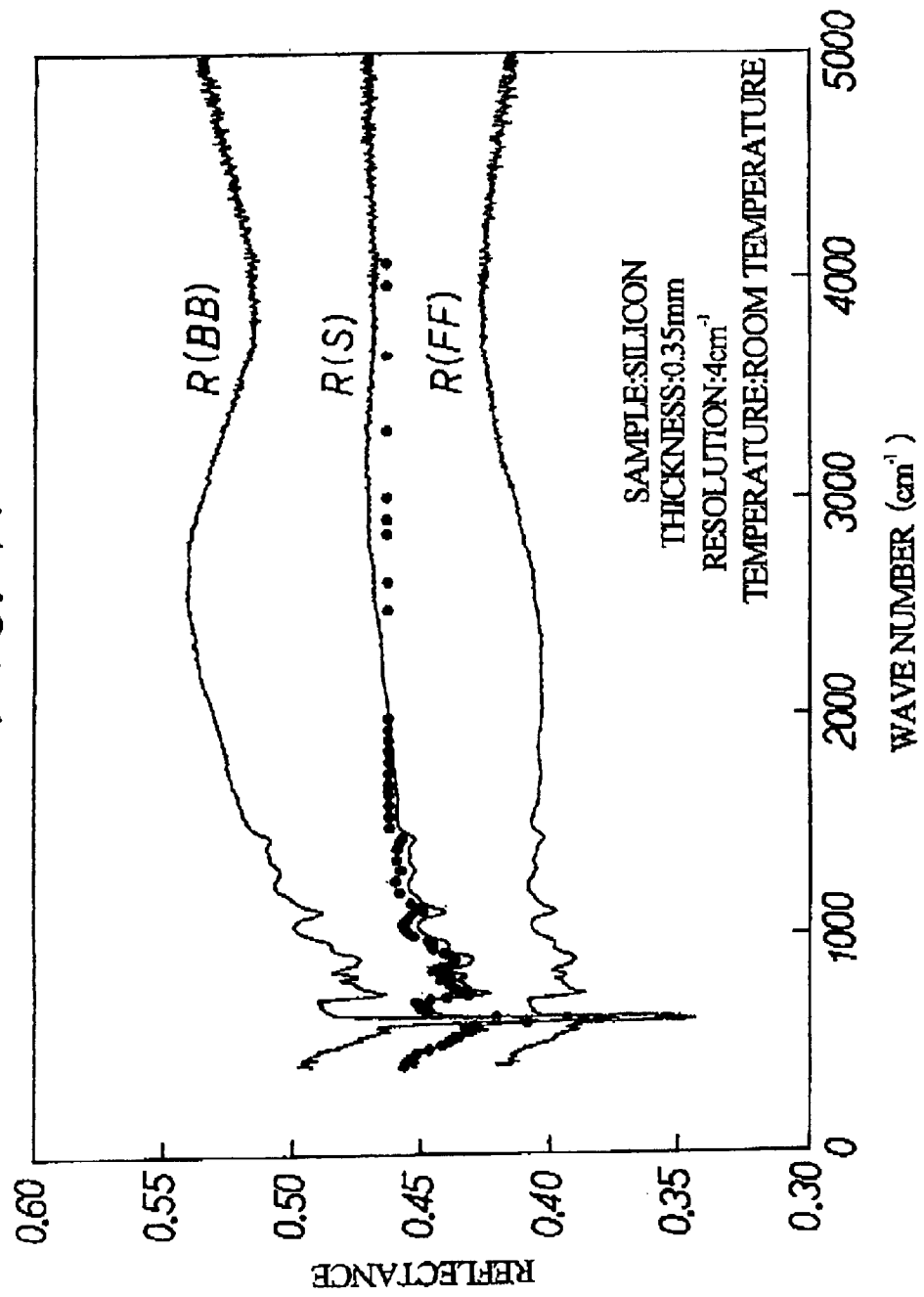
FIG. 11 is spectra showing the experimental result of the reflection spectra of a pure silicon sample by an optical system in accordance with the present invention.
Figure 12A:
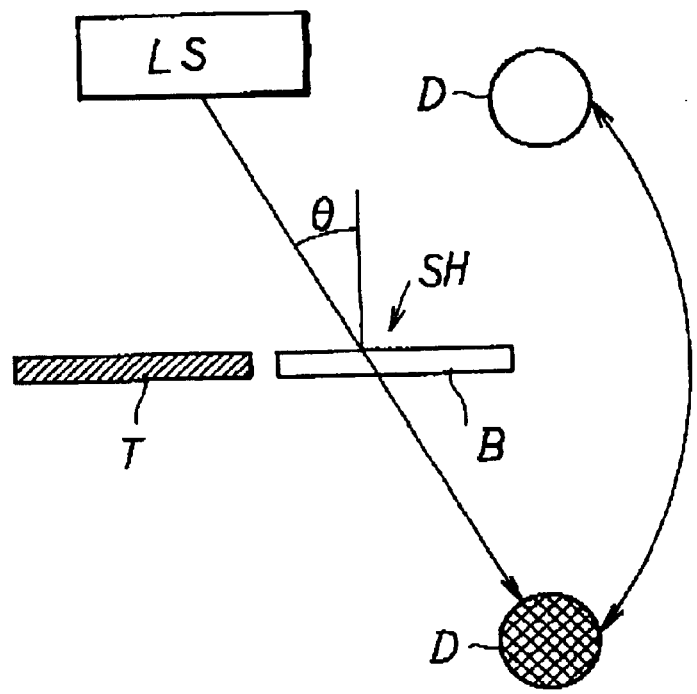
FIGS. 12A and 12B are schematic representations describing a method for measuring the absolute reflectance by a conventional goniometric method.
Figure 12B:
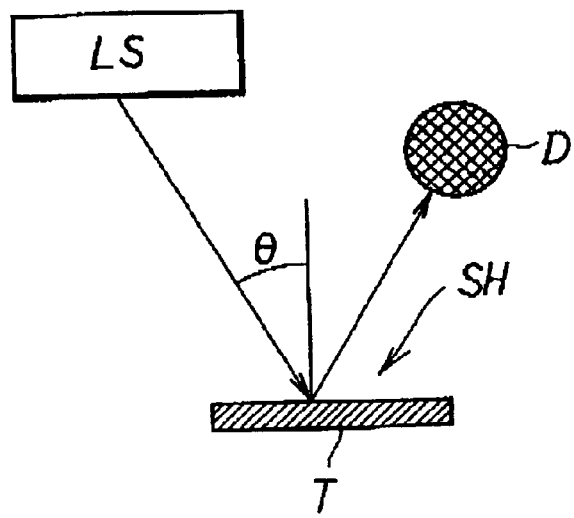

FIG. 11 shows the result of measurement of the reflectance of the same sample in the same measurement system. Upper and lower solid lines in the figure indicate the reflectance for the face side incidence and the back side incidence (R(FF) and R(BB)). In this case, the reflectance for the face side incidence is considerably deviated from the reflectance for the back side incidence (±8%). The reason therefor will be described below. In the description, how to obtain the geometric mean reflectance is also introduced below. The solid line in the vicinity of the center indicates this geometric mean reflectance (R(S)). The dots indicate the data calculated from the data book. This geometric mean reflectance and the reflectance indicated by the dots are coincident with each other within the measurement errors of ±0.4%.

In the measurement of two sets of reflectance for the face side incidence and the back side incidence, the measurement errors are considerably large of around ±8%. This is attributable mainly to four reasons described below.

(1) The incoming light from the light source of the spectrophotometer on the market into the beam switching mirror RM1 is deviated from the center-symmetrical shape of the Gaussian beam, and when this light is incident on the mirror of the optical system for measurement of optical constant, a part of the light is deviated from the mirror surface, and not reflected thereby, resulting in losses.

(2) By building a large number of mirrors in the optical system for measurement of optical constant, a part of the optical path is shielded by other mirrors, resulting in losses.

(3) In the measurement of the reflectance, separate sets of mirrors are used in the background measurement and in the sample measurement, and the reflectance of these mirrors is not the same.

(4) The diameter of the beam converged on the detector is larger than the diameter of the light receiving surface of the detector of the spectrophotometer on the market, resulting in losses.

For the reason (3) above, the reflectance of each mirror and the sample in FIG. 7 is denoted as R(RM1), R(RM2), R(SM1), R(SM2), R(SM3), R(SM4), R(CM1), R(CM2), R(CM3), R(CM4), and R(S), respectively. The reflectance of the mirrors in the detector unit 12b in FIG. 9 is denoted as R(2).

In addition, for the reasons (1), (2) and (4) above, the ratio of the light power which reaches the sample holder SH via RM1, SM21 and CM1 mirrors to the light power ($P_{in}$) incident on the beam switching mirror RM1 in FIG. 7 is defined as L1F, and the ratio of the light power which reaches the sample bolder SH via RM1, SM1 and CM2 mirrors to the $P_{in}$ in FIG. 7 is defined as L1B.

Next, the ratio of the light power which reaches the detector D via CM3, SM4 and RM2 and mirrors in the detection unit 2b in FIG. 9 to the light power incident on the samle holder SH is defined as L2F, and the ratio of the light power which reaches the detector D via CM4, SM3 and RM2 and mirrors in the detection unit 2b in FIG. 9 to the light power incident on the sample holder SH is defined as L2B.

The output $I_0$ in the background signal measurement for the face side incidence is expressed by the following formula.

$$I_0 = P_{in} \times R(RM1) \times R(SM2) \times R(CM1) \times L1F \times R(CM4) \times R(SM3) \times R(RM2) \times L2B \times R(2)$$

On the other hand, the output $I'_0$ of the background signal measurement for the back side incidence is similarly expressed by the following formula.

$$I'_0 = P_{in} \times R(RM1) \times R(SM1) \times R(CM2) \times L1B \times R(CM3) \times R(SM4) \times R(RM2) \times L2F \times R(2)$$

The output $I_r$ of the reflected sample signal measurement for the face side incidence is expressed by the following formula.

$$I_r = P_{in} \times R(RM1) \times R(SM2) \times R(CM1) \times L1F \times R(S) \times R(CM3) \times R(SM4) \times R(RM2) \times L2F \times R(2)$$

The output $I'_r$ of the reflected sample signal measurement for the back side incidence is similarly expressed by the following formula.

$$I'_r = P_{in} \times R(RM1) \times R(SM1) \times R(CM2) \times L1B \times R(S) \times R(CM4) \times R(SM3) \times R(RM2) \times L2B \times R(2)$$

The reflectance R(FF) to the face side incidence is defined as the ratio of $I_r$ to $\sqrt{I_0 \times I'_0}$, and the following formula is obtained.

$$R(FF) = \frac{I_r}{\sqrt{I_0 \times I'_0}} = R(S) \sqrt{\frac{R(CM1) \times R(CM3) \times R(SM2) \times R(SM4) \times L1F \times L2F}{R(CM2) \times R(CM4) \times R(SM1) \times R(SM3) \times L1B \times L2B}} \quad (1)$$

On the other hand, the reflectance R(BB) to the back side incidence is defined as the ratio of $I'_r$ to $\sqrt{I_0 \times I'_0}$, and the following formula is obtained.

$$R(BB) = \frac{I'_r}{\sqrt{I_0 \times I'_0}} = R(S) \sqrt{\frac{R(CM2) \times R(CM4) \times R(SM1) \times R(SM3) \times L1B \times L2B}{R(CM1) \times R(CM3) \times R(SM2) \times R(SM4) \times L1F \times L2F}} \quad (2)$$

From this result, generally speaking, R(FF)[1] R(BB). The product of R(FF) by R(BB) is equal to R(S)[2]. Thus, the absolute reflectance R(S) of the sample is determined as the geometric mean of two sets of actually measured reflectance, and expressed by the following formula.

$$R(S) = \sqrt{R(FF) \times R(BB)} = \sqrt{\left(\frac{I_r}{\sqrt{I_0 \times I'_0}}\right) \times \left(\frac{I'_r}{\sqrt{I_0 \times I'_0}}\right)} \quad (3)$$

R(FF), R(BB) and R(S) in FIG. 11 are determined from Formulae (1), (2) and (3), respectively.

In the reflectance measurement in which the optical system for measurement of optical constant is built in the spectrophotometer on the market, light losses are generated due to the above reasons, and two sets of reflectance R(FF) and R(BB) measured for the face side incidence and the back side incidence of a uniform sample are generally different from each other. Here, the following function IF defined as a root of the ratio of the reflectance R(FF) for the face side incidence to the reflectance R(BB) for the back side incidence of the uniform sample is introduced.

$$IF = \sqrt{\frac{R(FF)}{R(BB)}} = \sqrt{\frac{R(CM1) \times R(CM3) \times R(SM2) \times R(SM4) \times L1F \times L2F}{R(CM2) \times R(CM4) \times R(SM1) \times R(SM3) \times L1B \times L2B}} \quad (4)$$

This function is independent from the optical characteristics of the sample, and referred to as a device function.

The absolute reflectance $R_F(S)$ for face side incidence of the sample is expressed below by using the device function in the formula (4).

$$R_F(S) = R_f(S) = R(FF)/IF$$

The absolute reflectance $R_B(S)$ for the back side incidence is expressed below.

$$R_B(S) = R(BB) * IF$$

In a case of an ideal uniform sample, these two sets of the absolute reflectance $R_F(S)$ and $R_B(S)$ are equal to each other. On the other hand, in a case of non-uniform sample (for example, a thin film sample on the substrate), $R_F(S)$ and $R_B(S)$ are, generally, different from each other, and the optical constant of the thin film and the thickness of the thin film can be determined by simultaneously satisfying three results of measurement, i.e., these two results of measurement $R_F(S)$ and $R_B(S)$ and the result of measurement of the absolute transmittance.

As described above, the measurement time can be shortened to one half in the optical system for measurement of optical constant of each of the above embodiments, because there is no "replacement" for the optical system compared with the conventional optical measurement system. Accordingly, the sample need not be attached/detached, reproducibility of the measurement spectra is excellent, and the measurement accuracy can be improved. In addition, the absolute reflectance and the absolute transmittance can be measured without using any standard sample.

In addition, in this optical system for measuring optical constant, each of the measurement errors can be estimated from the difference between two sets of the absolute reflectance ($R_F(S)$ and $R_B(S)$) and the difference between the two absolute transmittances (t and t') in a case of the uniform sample. It can be determined from this error information that the optical measurement is performed correctly.

What is claimed is:

1. An optical system for measurement of an optical constant, comprising:
    an incoming side beam switching mirror configured to receive a light from a light source;
    first and second converged light reflecting means for forming first and second optical paths by projecting light from the incoming side beam switching mirror so as to be converged at an intersection of the first and second optical paths, the incoming side beam switching mirror being further configured to selectively switch a direction of the light received from the light source to the first or the second converged light reflecting means;
    a sample holder, said sample holder including a sample fitting hole and a through hole that are selectively advanced/retracted to/from the intersection of the first an second optical paths; and
    first and second received light reflecting means for projecting light to a single exiting side beam switching mirror, the first and second received light reflecting means being disposed on the optical path of the light reflected by or transmitted through a sample set in the sample fitting hole of the sample holder via said first or second optical path, or the through hole, and said exiting side beam switching mirror is configured to switch a direction of the light projected via said received light reflecting means so that the light is projected toward a single detector,
    wherein the absolute reflectance and the absolute transmittance for the face side incidence and the back side incidence of the sample can be measured therein.

2. The optical system of claim 1,
    wherein first and second converged light reflecting means and first and second received light reflecting means are ellipsoidal mirrors, respectively; and
    wherein each of the ellipsoidal mirrors can be disposed so that one focal point is located at the sample holder, the other focal point is on the optical axis of the incoming or exiting light, and the optical axes of the optical paths are within a single plane.

3. The optical system of claim 2,
    wherein each ellipsoidal mirror is disposed in an X-shape symmetry to the plane including a sample surface.

4. The optical system of claim 1,
    wherein said converged light reflecting means and received light reflecting means comprise first and second spheroidal mirrors;

wherein said spheroidal mirrors are coupled with each other at respective apertures thereof so that the axes of rotation and one of focal points thereof are coincident with each other, respectively;

wherein said sample holder is disposed at a common focal position of said spheroidal mirrors, and the incoming side beam switching mirror and the exiting side beam switching mirror are disposed at two remaining focal positions; and wherein an incoming through hole is opened on the incoming side of said first spheroidal mirror, and an exiting through hole is opened on the exiting side of said second spheroidal mirror, respectively.

5. The optical system of claim 4, wherein two beam switching mirrors are rotatable in a correlating manner with each other and the absolute reflectance and the absolute transmittance can be measured at an arbitrary angle of incidence.

6. The optical system of claim 4, wherein the beam switching mirror on the exiting side is independently rotatable to measure the light scattering by the sample.

7. The optical system of claim 4, wherein the incoming light on a thin film sample on a substrate is P-polarized light, and the angle of incidence on the sample can be set to the Brewster's angle with respect to the substrate by setting the rotational angle of two beam switching mirrors.

8. The optical system of claim 1, wherein said converged light reflecting means and said received light reflecting means are constituted by combining a concave mirror with supplementary mirrors;

wherein the concave mirror and the supplementary mirrors constituting the converged light reflecting means are disposed so that the light from the beam switching mirror on the incoming side is projected on the concave mirror via the supplementary mirrors, and projected toward the sample holder; and wherein the concave mirror and the supplementary mirrors constituting the received light reflecting means are disposed so that the light from the sample holder is projected on the supplementary mirrors via the concave mirror, and projected on the beam switching mirror on the exiting side.

9. The optical system of claim 8, wherein each concave mirror is disposed in an X-shape symmetry to the plane including the sample surface.

10. The optical system of any one of claims 1 to 9, being built in a dispersion type spectrophotometer or a Fourier transformation type spectrophotometer.

11. An optical system for measurement of an optical constant, comprising:

an incoming side beam switching mirror configured to receive a light from a light source;

first and second converged light reflecting means for forming first and second optical paths by projecting light from the incoming side beam switching mirror so as to be converged at an intersection of the first and second optical paths, the incoming side beam switching mirror being further configured to selectively switch a direction of the light received from the light source to the first or the second converged light reflecting means;

a sample holder, said sample holder including a sample fitting hole and a through hole that are selectively advanced/retracted to/from the intersection of the first and second optical paths; and first and second received light reflecting means for projecting light to a single exiting side beam switching mirror, the first and second received light reflecting means being disposed on the optical path of the light reflected by or transmitted through a sample or a reference sample set on the sample holder via said first or second optical path, and said exiting side beam switching mirror is configured to switch a direction of the light projected via said received light reflecting means so that the light is projected toward a single detector, wherein said converged light reflecting means and received light reflecting means comprise first and second spheroidal mirrors, wherein said spheroidal mirrors are coupled with each other at respective apertures thereof so that the axes of rotation and one of focal points thereof are coincident with each other, respectively, wherein said sample holder is disposed at a common focal position of said spheroidal mirrors, and an incoming side beam switching mirror and an exiting side beam switching mirror are disposed at two remaining focal positions, wherein an incoming through hole is opened on the incoming side of said first spheroidal mirror, and an exiting through hole is opened on the exiting side of said second spheroidal mirror, respectively, and wherein two beam switching mirrors are rotatable in a correlating manner with each other and the reflectance and the transmittance can be measured thereby at an arbitrary angle of incidence.

* * * * *